United States Patent [19]

Holly

[11] Patent Number: 4,518,579
[45] Date of Patent: May 21, 1985

[54] PH STABILIZED FLUORESCING OPHTHALMIC COMPOSITION CONTAINING FLUOREXON

[75] Inventor: Frank J. Holly, Lubbock, Tex.
[73] Assignee: Holles Laboratories, Cohasset, Mass.
[21] Appl. No.: 71,738
[22] Filed: Aug. 31, 1979
[51] Int. Cl.³ .................... G01N 31/00; G01N 33/48; A01N 43/90
[52] U.S. Cl. ........................ 424/9; 424/7.1; 436/172
[58] Field of Search ........................ 424/7.1, 8, 9, 253; 436/172

[56] References Cited

U.S. PATENT DOCUMENTS 3,306,820  2/1967  Krezanoski ............................ 424/7
3,374,144  3/1968  Stolar ................................... 424/7.1

FOREIGN PATENT DOCUMENTS 858019  1/1961  United Kingdom ................... 424/3

OTHER PUBLICATIONS

Refojo et al., J. Amer. Optometric Asso., vol. 43, No. 3, Mar. 1972, pp. 321-326.
Refojo et al., Arch Ophthal., vol. 87, Mar. 1972, pp. 275-277.
Norm, Acta Ophthalmologica, vol. 51, 1973, pp. 670-678.
Hoelzl Wallach, Anal. Chem., vol. 31, 1959, pp. 456-460.

Primary Examiner—Sam Rosen
Assistant Examiner—K. S. Moss
Attorney, Agent, or Firm—Robert L. Goldberg

[57] ABSTRACT

An ophthalmic composition for use in the human eye comprising an aqueous solution of fluorexon whose pH has been adjusted to between pH 5.4 and 6.2 to deliver maximum fluorescence and additionally containing sufficient buffer to maintain that pH even after instillation into the eye.

10 Claims, No Drawings

PH STABILIZED FLUORESCING OPHTHALMIC COMPOSITION CONTAINING FLUOREXON

BACKGROUND OF THE INVENTION

1. Field of the Invention

This invention relates to an ophthalmic compositions for use as a fitting or diagnostic aid, particularly for use with hydrogel contact lens.

2. Description of the Prior Art

It is well known in the prior art to use sodium fluorescein, commonly referred to simply as fluorescein, to evaluate the fit of contact lens and to evaluate the tear film and cornea prior to and following contact lens wear. Fluorescein is considered by most authorities to be an essential tool in making these evaluations. Desiccation, dry spots, epithelial defects, and certain other irregularities are difficult, if not impossible, to detect without the use of fluorescein.

Because of its absorption by hydrogel contact lens and its staining the lens, fluorescein can not be used for evaluating the fit of the hydrogel lens and, if it has been instilled for evaluation of the tear film and cornea, a certain amount of time must be allowed to elapse before a hydrogel lens can be inserted.

A one hour wait after using fluorescein is commonly recommended before such an insertion is made. This delay of an hour prior to hydrogel lens insertion is severely limiting to the practitioner and may not allow the use of fluorescein. Also, there is no direct way of evaluating the corneal-lens relationship as there is for hard lens with fluorescein. The need for a substitute fluorescein dye for use with hydrogel lens was apparent.

To overcome this problem, a new fluorescent water-soluble dye, fluorexon, was adopted for use with hydrogel lens.

Hydrophilic soft contact lens are made of polymers having a strong affinity for water. The polymeric macromolecules are interconnected by crosslinks forming 3-dimensional networks. The crosslinks render the polymer insoluble in all solvents. However, network polymers swell in good solvents, forming gels. When the swelling solvent is water, the material is termed a hydrogel. Hydrophilic soft lens are often referred to as hydrogel lens.

Hydrogel contact lens absorb aqueous solutions until swelling equilibrium is reached. The degree of swelling depends, for each given type of hydrogel contact lens, on its chemical composition, the degree of crosslinking, and on the compositon of the bathing solution.

Hydrogel lens consist of a polymer matrix containing interconnecting interstices of the network which are filled with an aqueous solution. The interconnecting interstices of the network are open to the surface of the lens, and it is proper to say that hydrogel lens are porous. Ions and molecules of dimensions smaller than the "pores" in the lens are easily absorbed into the lens. Through the pore size of the typical hydrogel lens, fluorescein can readily be absorbed. However, it was found that fluorexon was of larger dimensions and as such much less could be absorbed resulting in only negligible staining allowing its use with hydrogel lens without the accompanying disadvantages of transparency changes due to staining. The use of compounds such as fluorexon and fluorescein in these applications depends upon their ability to absorb light at characteristic wave lengths, which peaks for fluorescein at 490 nm and for fluorexon at 494 nm, and they emit light at longer wave lengths, which peaks in the case of fluorescein at 520 nm and fluorexon at 524 nm. A disadvantage in the prior art has been that a fluorescein solution 0.25% by weight in normal saline excited at wave length 490 nm, fluoresces twice as much as fluorexon of the same concentration. Because the molecular weight offluorexon (710) is almost twice as large as the molecular weight of fluorescein sodium (376), at the same weight percent concentration, almost twice as many molecules of fluorescein as fluorexon will be present in equal volume of both solutions. But, even in solutions of the same molar concentration, 0.47% by weight fluorexon and 0.25% by weight fluorescein, the fluorescence of fluorexon is still about 50% lower than the fluorescence of fluorescein. This happens because, at these relatively high levels of concentration, fluorescence does not increase linearly with increasing concentration. In other words, it is impossible to increase the concentration of fluorexon to a level where its degree of fluorescenceequals that of a 0.25% by weight solution of fluorescein.

Accordingly, while fluorexon which stains hydrogel lens slowly and gradually and is easily reversible, is preferred over fluorescein which stains hydrogel lens easily and intensively, the lower fluorescene of fluorexon has been one of the reasons for its limited adoption by practitioners in the art. Thus, a need exists for a means of increasing the relative fluorescence of fluorexon and maintaining that increased level of fluorescence even after its addition to the eye. As stated above, merely increasing the concentration of fluorexon is not a complete answer since the fluorescence does not increase linearly, fluorexon has only limited solubility in water, and because it is desirable to reduce the concentration of materials put into the eye due to the potential for irritation.

SUMMARY OF THE INVENTION

The present invention comprises an aqueous solution of fluorexon which has been pH adjusted to deliver maximum fluorescence and additionally contains a buffer to maintain that pH even after instillation into the eye.

DETAILED DESCRIPTION OF THE INVENTION

The fluorescing material of the present invention is bis(N,N-bis(carboxymethyl)-aminoethyl)-fluorescein tetrasodium salt (fluorexon). Fluorexon has been used in the past as an indicator in the laboratory titration of calcium. It is commercially available as a yellow powder. While it is possible to use the fluorexon as it is obtained from the supplier, it is preferred that various contaminants be removed from the fluorexon by adding the crystalline fluorexon to ethyl alcohol at a ratio of about 1:20, stirring for several minutes and then filtering through a Whatman 2V filter which results in the purified fluorexon crystals being retained by the filter paper with the contaminants being carried away by the ethyl alcohol.

The fluorexon is dissolved in water at a concentration by weight of between about 0.01% and about 2.0%, preferably between about 0.35% and about 0.60%. In contrast to the prior art, where concentrations of 0.6% and greater were required due to the lesser relative fluorescence of fluorexon as compared to sodium fluorescein, it has been found that by varying the pH it is possible to increase the relative fluorescence of fluorexon. Accordingly, by varying the pH it is possible to decrease the concentration of fluorexon in the composition while maintaining a suitable level of fluorescence. The pH of the composition is preferably adjusted to obtain the maximum fluorescence. While this pH is more acidic than that of the tearfilm covering the preocular surface, it is still less acidic than that of the skin surface and has been found to be tolerated well in the eye. It is preferred that the pH be adjusted to between about 5.4 and 6.2, preferably between about 5.8 and about 6.0, most preferably 5.9. The pH of the solution may be adjusted by adding one or more of the acids or bases known for use in ophthalmic solutions. An aqueous solution of fluorexon is acidic requiring the addition of a base, a preferred base being sodium hydroxide.

Since the pH of the tearfilm coveringthe preocular surface of the human eye differs from that of a solution of fluorexon which has been adjusted for maximum fluorescence such that dilution by the tears in the eye will change the pH of the composition somewhat, the composition should be buffered to maintain the desired pH and therebymaintain the maximum amount of fluorescence. Any of the buffers previously used in ophthalmic preparations are suitable for the present invention including phosphates, acetates, carbonates, and citrates provided the combinations are compatible with the eye. For the preferred range of pH between 5.8 and 6.0, the preferred buffer is phosphate, i.e. a mixture of monobasic and dibasic phosphate salts, ranging in molar ratio between about 13.9:1 and about 8.9:1, at a total phosphate molarity of about 0.1. Such a concentrated buffer is nearly isotonic. The total phosphate concentration in the buffer could range from this maximum molarity of about 0.1M to about 0.005M, with a concurrent change in the ratio of monobasic to dibasic phosphate being needed in order to correct for the pH shift that occurs upon dilution. At this twenty-fold dilution, the buffer capacity of the phosphate solution is still somewhat greater than that of the tears. However, at this low concentration, the osmolality of the buffer is negligibly small.

If pH values lower than 5.7 are desired, then a mixture of sodium acetate and acetic acid is the preferred buffer. At pH 5.4, the molar ratio of salt to acid is 4.8:1 at a total acetate concentration of 0.18M, which is about isotonic. The method of preparation of various other buffers suitable forophthalmic formulations is well known to those skilled in the art.

It is preferred that the ophthalmic solution of the present invention be isotonic. Since the salts used to prepare the buffer are usually present at insufficient levels to render the solution isotonic, any of the salts described as useful in the prior art for rendering an ophthalmic solution isotonic may be used in the present invention to increase osmolality to isotonic levels, such as, for example, sodium chloride, potassium chloride, calcium chloride, magnesium chloride, and various sulfates, phosphates, borates, nitrates, citrates, acetates, etc.

If desired, it is also possible to add a preservative to the ophthalmic solution used in the present invention. For example, biocides such as benzalkonium chloride, thimerosal, phenylmercuric nitrate, chlorobutanol, methyl paraben, propyl paraben, chlorhexidine digluconate, and sorbic acid and chelating agents, such as, for example, di, tri, or tetrasodium ethylene diamine tetraacetate, also known as edetates, may be added at concentrations between about 0.001% and 1.0% by weight.

In addition, the composition of the present invention can also contain as an optional ingredient an eye compatible anesthetic such as, for example, benoxinate, butyl-4-aminobenzoate, naepaine, and phenacaine. A preferred anesthetic is proparacaine. The following example is given by way of illustration only and is not to be considered as limiting the scope of the invention.

EXAMPLE I 25 grams of fluorexon crystals (Aldrich Chemicals) were added to 500 milliliters of absolute ethanol. The solution was stirred for 60 minutes, after which time the undissolved fluorexon crystals were recovered by straining the solution through a Whatman 2V filter. The crystals were removed from the filter paper and allowed to dry.

To 5 liters of deionized water were added 17.50 grams of purified fluorexon. To this was added 39.75 grams of potassium phosphate monobasic and 5.80 grams of sodium phosphate dibasic. Next, 20.50 grams of sodiumchloride were added to make the composition isotonic. At this point the pH of the solution was checked with the pH meter and was determined to be between 3.8 and 3.9. To the composition was added a sufficient amount of 1 N sodium hydroxide to bring the pH up to the desired value.

The fluorescence of the resulting solution is measured by a fluorophotometer system, which consists of a dissecting microscope, a photomultiplier tube, an Amicon photomultiplier photometer, and a light source. The fluorescence is measured by pipetting an aliquot of solution into a polyethylene trough of exact dimensions, which is placed on a black support in the visual fleld of the microscope and is illuminated with blue light at the excitation wave length of fluorexon, 494 m$\mu$ by means of a fiberoptic cable connecting a Dyonics light source to the left eyepiece of the microscope. The light reflected from the trough is picked up by a fiberoptical probe placed in the right eyepiece of the microscope, passed through a filter, so that only the emission wave length of fluorexon, 524 m$\mu$ is allowed through. This light is then conducted through a fiberoptic cable to the photomultiplier tube, which amplifies the signal electronically. The signal is measured by the photomultiplier photometer. The focusing is adjusted until maximum light intensity is measured for the sample. The measurements are made in a dark room, the only illumination coming from a red lamp, to obtain maximum sensitivity.

Table I below illustrates the pH dependence of a 0.35% fluorexon solution measured as described above, the pH having been adjusted to the appropriate value by adding 1N sodium hydroxide.

TABLE I

| pH | Relative Fluorescence |
| --- | --- |
| 5.20 | 13.2 |
| 5.45 | 14.7 |
| 5.90 | 15.3 |
| 6.15 | 14.8 |
| 6.35 | 13.8 |
| 6.60 | 12.9 |
| 7.10 | 11.7 |
| 7.40 | 11.4 |

While the table shows the relative fluorescence for a solution of 0.35%, corresponding increases will be seen regardless of the relative concentration of fluorexon in the composition.

The prepared solution can be used for fitting contact lens by placing a drop of the fluorexon solution on the concave, inner surface of the lens and then placing the lens on the eye. The fluorescent tearfilm can be readily observed between the lens and the cornea. Observation is best made with a strong black light source and the naked eye or loupe rather than with the biomicroscope since it is desirable to make the initial observation prior to blinking. Other comparable procedures for use in fitting contact lens are well known in the prior art.

Other embodiments of the invention will be apparent to those skilled in the art from a consideration of this specification or practice of the invention disclosed herein. It is intended that the specification and example be considered as exemplary only, with the true scope and spirit of the invention being indicated by the following claims.

What is claimed is:

1. An ophthalmic solution for use in a human eye comprising an aqueous solution of fluorexon, the solution having a pH between about 5.4 and about 6.2, and sufficient eye compatible buffer to maintain said pH after said solution is instilled into the eye.

2. The ophthalmic solution of claim 1 in which said pH is between about 5.8 and about 6.0.

3. The ophthalmic solution of claim 1 in which said fluorexon is present in a concentration by weight of between about 0.0% and about 2.0% by weight.

4. The ophthalmic solution of claim 1 in which said buffer is present in a concentration between about 0.005M and about 0.1M.

5. The ophthalmic solution of claim 1 in which said buffer is a combination of potassium phosphate monobasic and sodium phosphate dibasic.

6. The ophthalmic solution of claim 1 in which said ophthalmic solution comprises, in addition, an eye compatible anesthetic.

7. The ophthalmic solution of claim 6 in which said anesthetic is proparacaime.

8. The ophthalmic solution of claim 1 in which said ophthalmic solution comprises, in addition, one or more cationic salts at a level sufficient to provide an isotonic solution.

9. An ophthalmic solution for use in a human eye comprising an aqueous solution containing about 0.35% by weight fluorexon, the solution having a pH of between about 5.8 and about 6.0, and the solution containing about 1% by weight of a combination of potassium phosphate monobasic and sodium phosphate dibasic in a ratio of about 6:1.

10. A method of fitting hydrogel contact lens in a human eye comprising instilling an aqueous solution of fluorexon the solution having a pH between about 5.4 and about 6.2, and sufficient eye compatible buffer to maintain said pH after said solution is instilled into the eye, and examining said eye and lens with a light of an appropriate wavelength.

* * * * *